United States Patent [19]

Baran et al.

[11] 4,423,725
[45] Jan. 3, 1984

[54] MULTIPLE SURGICAL CUFF

[76] Inventors: Ostap E. Baran; Andrij O. D. Baran, both of 219 E. 12th St., New York, N.Y. 10003

[21] Appl. No.: 363,872

[22] Filed: Mar. 31, 1982

[51] Int. Cl.$^3$ ............... A61M 16/00; A61M 25/00; A61M 7/00
[52] U.S. Cl. ............................. 128/207.15; 604/43; 604/101
[58] Field of Search .................. 128/200.26, 203.1 R, 128/207.14, 207.15, 4, 656, 658; 604/96, 101, 102, 43, 45, 95

[56] References Cited

U.S. PATENT DOCUMENTS

| | | | |
|---|---|---|---|
| 2,642,874 | 6/1953 | Keeling | 604/101 |
| 2,854,982 | 10/1958 | Pagano | 604/101 |
| 3,173,418 | 3/1965 | Baran | 128/207.15 |
| 3,411,506 | 11/1968 | Velasco | 604/101 |
| 4,066,070 | 1/1978 | Utsugi | 604/95 |
| 4,211,233 | 7/1980 | Lin | 604/43 |
| 4,230,119 | 10/1980 | Blum | 604/101 |
| 4,248,221 | 2/1981 | Winnard | 128/207.15 |

Primary Examiner—Henry J. Recla
Assistant Examiner—Karin M. Reichle
Attorney, Agent, or Firm—S. C. Yuter

[57] ABSTRACT

A multiple surgical cuff for introduction into a body passage such as a trachea, bladder and urethra opening or artery comprising a tubular base member encircled by proximal, distal and middle double cuff members. The middle double cuff member comprises an inflatable tubular inner cuff member encircled by a distensible tubular outer cuff member, whose wall is multiperforated at spaced points. Separate passage means communicate with each cuff member so that each can be inflated to press against the adjacent portion of the body passage wall. Another passage communicates with the space between the inner and outer cuff members of the middle double cuff member to permit the introduction of a surgical fluid such as an anesthetic in that space, so that expansion of the inner cuff member forces the fluid onto the adjacent portion of the wall of the body passage. Still another passage communicates with the space along the tubular base member between the middle and proximal cuff members and permits the introduction of a surgical fluid, such as a cleansing saline solution, or to suck out loose thicker material from there and also enables continuous cooling and washing by an inflow and separate outflow. A plurality of side window openings in the tubular base member on the near side of the proximal cuff member permits the continued flow of blood when the body passage is an artery and continued flow is indicated.

10 Claims, 5 Drawing Figures

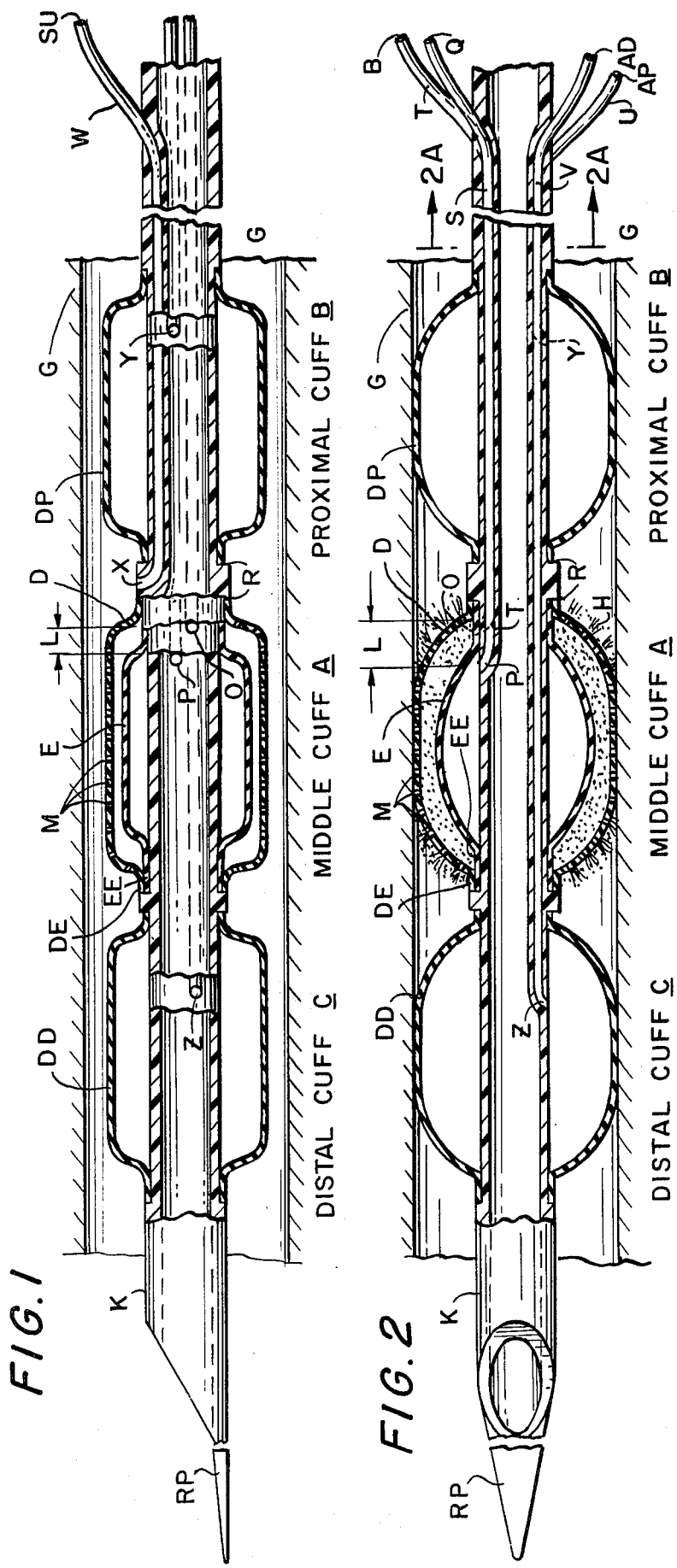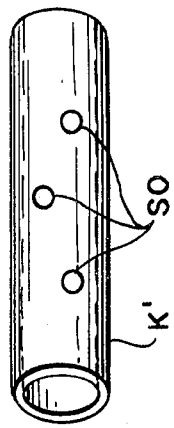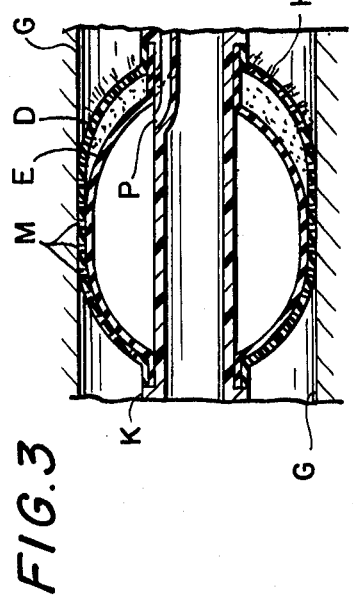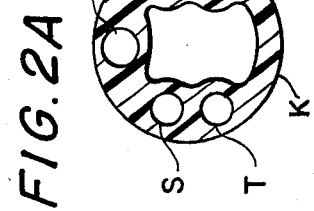

MULTIPLE SURGICAL CUFF

FIELD OF THE INVENTION

This invention relates to improved surgical cuffs and, more particularly, to an improved double-wall endotracheal cuff which is the subject of U.S. Pat. No. 3,173,418 issued Mar. 16, 1965 to joint inventor Ostap E. Baran, M.D. ("the 1965 patent").

BACKGROUND OF THE INVENTION

The invention disclosed in the 1965 patent relates to a double-wall endotracheal cuff, the external wall of which is multiperforated for the administration of continuous or intermittent local endotracheal anesthesia. The very same cuff may be very advantageously employed for endo-esophageal, endo-stomach, endo-duodenal, or pharyngeal surface anesthesia as well as surface anesthesia in any other cavity in the body, as well as for other necessary medicaments.

The problem which anesthetists and surgeons have encountered in the use of endotracheal anesthesia, and which the invention of the 1965 patent solved, is that shortly (about three quarters of an hour or sooner) after injection of anesthetic into the trachea and placing of the endotracheal tube, the anesthetic wears off or is destroyed and the patient is thereafter unable to endure the presence of the tube in the trachea. The patient starts to cough and vomit, making it difficult for the surgeon to perform the operating procedure. Attempts had been made, prior to the invention of the 1965 patent, to solve this problem by use of deep anesthesia administered to such level that the patient loses all endotracheal feeling and reflexes. Frequently this unnecessarily intoxicated the whole body system and often endangered the life of the patient, especially in the presence of damage to the cardio-vascular system, liver, kidney, lungs or brain centers.

The invention of the 1965 patent is a double-wall endotracheal cuff for continuous or intermittent local endotracheal anesthesia around the endotracheal tube which enables the patient to tolerate the endotracheal tube, not only during the light-superficial stage of general anesthesia but also in the absence of general anesthesia when the patient is awake. The invention could be life saving in conditions such as tetanus or bilateral pneumonia when a continuous free passage of oxygen to the lungs and suction of exudate from the lungs represent most important factors for a successful recovery.

While the invention of the 1965 patent was a major improvement in the anesthetic art it did not solve all of the problems. Moreover, it generated a demand for an even better surgical cuff.

One of the problems was the possibility of ischemic necrosis on the airway wall due to excess or prolonged pressure on the wall.

Another problem was that drugs could spill over to the healthy area of a body passage and do unnecessary damage.

Still another problem was the prolonged accumulation of a drug in the area treated to the point where its removal would be beneficial to the patient.

SUMMARY OF THE INVENTION

Thus, the principal object of our new invention is to solve these and other problems presented by the invention of the 1965 patent and similar surgical cuffs.

Another object of our invention is to provide an improved double-wall surgical cuff.

A specific object of our invention is to expand the use of a surgical cuff to procedures involving the continued flow of blood through a passage.

Still another object of our invention is to provide an improved means for widening arteries and/or enable application of surgical fluid on the specific limited body surface or artery, or for radial dilatation of strictures of the body passges.

Briefly, these and other objects of our invention are achieved by a multiple surgical cuff for introduction into a body passage, such as a trachea, bladder opening, urethra or artery, comprising a tubular base member encircled by proximal, distal and middle double cuff members. The middle cuff member preferably comprises an inflatable tubular inner cuff member encircled by a distensible tubular outer cuff member whose wall is multiperforated at spaced points. Separate passage means communicate with each cuff member so that each can be inflated to press against the adjacent portion of the body passage wall. Another passage communicates with the space between the inner and outer cuff members of the middle double cuff member to permit the introduction of a surgical fluid in that space, so that expansion of the inner cuff member forces the fluid onto the adjacent portion of the wall of the body passage. Still another passage communicates with the space along the tubular base member between the middle and proximal cuff members and permits the introduction of a surgical fluid, such as a saline solution to cleanse the adjacent area, or to suck out loose thicker material from there; or, alternatively, continuous inflow via the passage which communicates with the space between the inner and outer cuff members and continuous outflow via the cleansing passage. Such continuous flow permits continuous cooling of the adjacent portion of the wall of the body passage; also continuous visibility of the fluid color to inform the surgeon of the bleeding condition of the adjacent wall portion.

A feature of our invention is a plurality of side window openings in the tubular base member on the near side of the proximal cuff to permit the continued flow of blood through an artery when that is indicated.

An advantage of the invention is that different therapeutic drugs may be evenly sprayed into the space between the distal and proximal cuffs when they are inflated to sealing contact with the body passage.

Another advantage when the distal and proximal cuffs are in sealing contact with the body passage is that drugs may be administered under pressure forcing such drugs to penetrate deep into the tissue or gland ducts located in the sealed segment after proper dilatation of the passage.

Another advantage in airway pathology is the ability to administer low dosage with high concentration of toxic drugs locally-for example, during local chemotherapy of the larynx, trachea and larger bronchus—without spilling of the drugs to the healthy area.

Still another advantage is that, when desirable, drugs may be removed by sucking out with a syringe, or the sealed area may be continuously washed out with a normal saline solution.

Yet another advantage of our invention is the ability to control bleeding of the esophageal varicose vein in the cardia area.

The risk of ischemic necrosis on the airway wall due to excess or prolonged pressure is very substantially reduced by intermittently inflating each cuff separately to avoid pressure on one segment of the body passage, or by using less pressure in each of the three cuffs at the same time.

An advantage in urology is the ability to create a closed space of the prostatic urethra and inflate the middle cuff to dilate the prostatic urethra, which often is narrowed by an enlarged prostate or even pathologically closed by strictures. That avoids all of the consequences of urinary tract retention. Moreover, the invention permits massage of the prostate from the urethra by inflating and deflating the middle cuff using locally greater and externally controlled pressure.

Another advantage in urology is that x-ray contrast drugs may be forced deep into the multiple and very thin prostatic gland ducts-tree to substantially enhance x-ray diagnosis of the pathological structure of the prostate gland and to enable the performance of prostatography of the ducts and their branches after the first proper dilatation of the urethra and prostate gland.

Still another advantage in urology is that local hormonal or chemotherapy may be performed through the prostatic gland ducts using smaller amounts of drugs but in greater concentration in the treatment of a benign or malignant hypertrophy of the prostate. That causes shrinkage of the gland while avoiding bloody surgery or feminization of the entire body, by using oral or injectable estrogenic hormones as heretofore practiced.

An advantage of the invention in treating cardio-vascular diseases is, in angioplasty for example, the ability, after the atheromateous substance is squeezed laterally by the middle cuff, and the cuff deflated, to wash out all of the cholesterol debris and inject local anticoagulant drugs, or use cholesterol diluting drugs, in the tightly sealed segmental area only.

BRIEF DESCRIPTION OF DRAWING

Other objects, features and advantages of our invention will be apparent from the following detailed description of the invention taken together with the accompanying drawing wherein:

FIG. (FIG.) 1 is a side view, partly broken away and in section, of an improved deflated multiple surgical cuff, in accordance with the preferred embodiment of the invention, mounted permanently on the tubular base member.

FIG. 2 is a similar view, with the tubular base member and multiple cuff rotated 90 degrees from the FIG. 1 position, showing the distal and proximal cuffs inflated to seal a segment of the internal wall of the trachea and the partially inflated internal cuff of the middle cuff forcing anesthetic drugs onto the internal wall of the trachea through openings in the external multiperforated cuff of the middle cuff.

FIG. 2A is a section along the line 2A—2A of FIG. 2 showing the air, surgical fluid and suction communication passages passing through the wall of the endotracheal tube.

FIG. 3 is a similar view of the middle cuff showing the internal cuff inflated to press the external cuff into sealing relation with the internal wall of the trachea while, simultaneously, spraying anesthetic proximally only.

FIG. 4 is an elevational view of a section of a multiple cuff supporting tube on the near side of the proximal cuff showing the side window openings for passage of blood through the lumen of the tube when used in arterial surgical procedures.

DETAILED DESCRIPTION OF THE INVENTION

The specification and drawings of the 1965 patent are hereby incorporated by reference, and corresponding elements in this description are designated by the same reference characters as the 1965 patent.

Referring to the improved multiple surgical cuff shown in FIGS. 1, 2 and 2A permanently mounted on an endotracheal tube K, which is inserted into a trachea adjacent internal trachea wall G, middle double cuff A, proximal cuff B and distal cuff C encircle endotracheal tube K.

Middle double cuff A comprises internal cuff E, which encircles endotracheal tube K, and external multiperforated cuff D, which encircles internal cuff E. The end portions EE of internal cuff E and the end portions DE of external cuff D are adheredly mounted in recesses R in the endotracheal tube K. End portions EE and DE at the far end are substantially coextensive. However, at the near end, end portion DE is displaced a distance L (about one centimeter) from end portion EE. Internal cuff E and external cuff D are made of rubber (or similar material) with external cuff D having multiperforations M.

Middle air canal T has an opening B at the near end and an opening P at the far end through which air is pumped to inflate internal cuff E. Anesthetic canal S has an opening Q at the near end and an opening O at the far end through which anesthetic (or other surgical fluid) may be pumped into the space between internal cuff E and external cuff D.

Proximal cuff B comprises cuff DP which is adhered to the endotracheal tube K the same way as external cuff D of middle double cuff A. Proximal air canal U has an opening AP at the near end and an opening Y at the far end through which air may be injected to inflate proximal cuff B.

Distal cuff C comprises cuff DD which is adhered to the endotracheal tube K the same way as external cuff D of middle double cuff A. Distal air canal V has an opening AD at the near end and an opening Z at the far end for injecting air into distal cuff C to inflate it.

Suction canal W has an opening SU at the near end and an opening X at the far end, along the endotracheal tube K between the middle double cuff A and proximal cuff B. Suction canal W permits the removal by suction of loose thicker material in the adjacent area as well as the introduction of a surgical fluid such as a saline solution to cleanse the area.

Middle cuff A is a double-walled cuff which functions as described in the 1965 patent. That is, anesthetic fluid may be injected into the space between internal cuff E and external cuff D via anesthetic canal S. Then air is pumped into internal cuff E via middle air canal T to inflate cuff E so that it presses the anesthetic H (FIG. 2) through the multiperforations M in the external cuff D onto the adjacent area of the internal wall G of the trachea. When the internal cuff E is fully inflated it presses external cuff D against the internal wall G of the trachea (FIG. 3) to seal the trachea at that segment. That situation makes it possible for the anesthetist to produce positive pressure in the lungs or perform artificial breathing for the patient by pressing and reducing the pressure on the rebreathing bag.

Alternatively, anesthetic may be gravity fed, drop by drop, into the space between internal cuff E and external cuff D to replace the used anesthetic.

If the anesthetist has some reason to limit the anesthesia to the proximal part of the trachea, the larynx and the pharynx, then after full inflation of the internal cuff E (FIG. 3) injected anesthetic fluid H enters the external cuff D through its separate opening Q, anesthetic canal S and opening O and is accumulated proximally. Since the external cuff D extends a distance L of about one centimeter farther proximally beyond the internal cuff E, local anesthetic is sprayed through multiple openings M around the proximal airway only, and by lowering the upper part of the body only (Trendelenburg position), the anesthetic fluid flows into the larynx and pharynx, anesthetizing that area.

The modus operandi relating to double middle cuff A is as follows:

After local spraying of the anesthetic into the pharynx and general induction of anesthesia, together with injection of relaxant drugs, and properly oxygenating the patient, the endotracheal tube K, with its double middle cuff A, is inserted into the trachea. Immediately 2 or 3 cc. of Cyclaine or other local anesthetizing agent are injected into the space between the internal cuff E and external cuff D through opening O. Under fluid pressure from the anesthetic and pressure from the distended internal cuff E due to pumped air, the external cuff D is stretched, the small multiple holes M are opened and the anesthetic H is sprayed through them around the endotracheal tube K and on the endotracheal mucous membrane, flowing down the tracheobronchial tree or into the pharynx according to the position of the patient.

Usually in about 45 minutes to an hour the anesthetic fluid is absorbed or destroyed and the patient may react to the presence of the endotracheal tube K in the trachea. To prevent that reflex, additional air pressure is put on external cuff D to further distend it, further spraying anesthetic H and the local endotracheal anesthesia is thereby prolonged.

Instead of intermittent injection of anesthetic H it is possible to maintain a continuous local endotracheal anesthesia by continuously dropping local anesthetic into the external cuff's canal S, as is done in intravenous medication.

In this manner there is the possibility not only of continuously maintaining the local anesthesia, but by continuous absorption of the local anesthetic it may be possible through the blood circulation to support general anesthesia, thereby avoiding cardio-vascular reflexes. This may be done, for example, by the use of Procaine or Pronestyl during some cardio-vascular operations.

A further advantage of this kind of anesthesia is that local anesthesia of the larynx reduces the danger of laryngo-spasms.

The advantages of using the middle cuff A explained above are inherent in the present invention as in the invention of the 1965 patent. Additional advantages from improvements, mainly the addition of the proximal cuff B, the distal cuff C and the suction canal W, will be seen in the following description of the operation of the multiple surgical cuff.

By inflating both proximal cuff B and distal cuff C to seal the segment of the wall of the trachea between them, different therapeutic drugs may be administered exclusively to the space between them. A further advantage is that the drugs may be administered under pressure forcing the drugs to penetrate deep into the tissue located at that segment after closing of suction canal W.

In airway pathology the invention makes it possible to administer low dosage with high concentration of the toxic therapeutic drugs locally only; for example, in larynx, trachea or larger bronchus procedures. This is accomplished without unnecessarily and disadvantageously spilling of the drugs to the healthy areas. When it is desirable the drug may be removed by sucking it out with a syringe via suction canal W, or even continuously washing it out with normal saline via inflow through opening O and outflow through opening X and suction canal W. That has not been previously possible to our knowledge.

The anesthetist may also intermittently inflate each of the three separate cuffs, avoiding pressure on one segment of the trachea. Alternatively, all three cuffs may be inflated at the same time but using less pressure in each cuff to obtain effective tight closure of the airway. Since pressure is then distributed on a larger surface, there is, consequently, less pressure on capillary circulation and less possibility of ischemic necrosis of the airway wall.

For use in urology, the multiple surgical cuff is sized appropriately, with a proportional supporting tube replacing endotracheal tube K and, preferably, with the addition of a rounded point RP at the distal end.

The multiple cuff is inserted into the urinary bladder far enough so that the distal cuff C passes the internal opening of the urethra. Then the distal cuff C is inflated to close the bladder opening internally (ostium urethra internum). The proximal cuff B, which should be located just below the external sphincter of the urethra in the parts membracea (3–4 centimeters from the distal cuff C), is inflated; then the middle cuff member is inflated and deflated repeatedly to dilate and massage the prostatic urethra. The prostatic urethra is often narrowed by an enlarged prostate or even pathologically closed by strictures, with all of the negative consequences of urinary tract retention.

Since the prostatic portion of the urethra has many very small openings of the tiny prostatic gland ducts, the tightly closed segment of urethra permits the injection of X-ray contrast drugs under pressure to force such drugs deep into the prostatic glands ducts-tree so that the X-ray picture will show healthy or pathological structure of ducts and the gland. That is, our invention permits the performance of prostatography of the gland ducts and their branches, believed not previously possible.

Additionally, local hormonal or chemotherapy may be performed through the prostatic gland ducts using less hormones or chemical drugs because our invention permits greater concentration of drugs only locally in the treatment of benign or malignant hypertrophic prostate. Thus shrinkage of the prostatic gland may be achieved avoiding bloody surgery or ferminization of the entire body as it heretofore has been practiced.

Our invention is also very useful in the treatment of cardio-vascular diseases, and especially to perform percutaneous-transluminal angioplasty of the arteries in the peripheral vascular atheromatous obstructive disease. In this procedure the multiple cuff is inserted into the artery to bracket the narrowed area between the proximal cuff B and the distal cuff C, which are then inflated. Then the internal cuff E is inflated to squeeze the atheromatous substance laterally. Because the substance is to some extent soft squeezable and not elastic, repeated pressure on the substance can restore widening of the artery with improved distal circulation. But often there is rupture of the intima membrane and dissection by the blood stream of the distal arterial tissue, with embolization of distal tissue by debris of the cholesterol deposits, secondary arterial ulceration and clot formation. If that distal tissue represents the brain or the heart muscle the risk to the patient is quite substantial. With the multiple cuff invention not only angioplasty may be performed but after deflation of the middle cuff A all of the cholesterol debris may be sucked out via suction channel W and anticoagulant drugs, like heparin, or cholesterol diluting drugs, may be applied exclusively to the sealed segm area, and in that way angio-chemoplasty may be performed avoiding distal embolization.

It should be understood that the longitudinal dimension of the middle cuff A and spacing of the three cuffs may be varied to accommodate different longitudinal dimensions of the pathological segment in the artery.

That procedure is convenient in peripheral vascular disease of the lower or upper extremities since ischemia may be tolerated for one half to one hour. However, in the heart arteriosclerosis or in the carotid arteries or brain arteries prolonged closure of the blood circulation will be deleterious to the heart or brain tissue. To avoid that problem an optional feature of our invention is the provision in the central cuffs-supporting tube K' on the near side of the proximal cuff B of side window openings SO (FIG. 4) communicating with the central lumen of the cuff-supporting tube K'. Openings SO permit blood to continuously circulate through the tube K', in that way avoiding prolonged ischemia of the distal tissue.

In case of the coronary, carotid or brain arterioplasty, side openings SO should be located at the level of the aorta to create the highest blood pressure and to prevent the side openings SO from being closed laterally by an adherent small artery wall.

Another important use of our invention is to treat acute bleeding from the lower end of the esophagus. Heretofore, such acute bleeding has been treated with the Blakemore-Sengstaken esophageal-nasogastric tube having two inflatable cuffs encircling a tube. The lower cuff after inflation closes the esophagus from the stomach side. The higher cuff after inflation puts pressure above the cardia in the lower end of the esophagus. The purpose of the pressure from the two inflated cuffs is to stop the bleeding. However, there is no way to apply direct pharmaceutical treatment to the varices and no direct radial centrifugal pressure between the two cuffs; or continuous local washing.

In accordance with our invention pressure can be applied below and above the cardia as well as at the level of the cardia via the distal cuff C, the proximal cuff B and the middle double cuff A. In addition, different pharmaceutical agents—such as vasoconstrictors, antibiotics and bacteriocidal drugs—may be applied to the bleeding segment via the anesthetic canal S, the space between the internal cuff E and the external multiperforated cuff D and the multiperforations M when the internal cuff E is expanded.

Further, the bleeding segment may be irrigated by cool saline solution and debris removed via the suction canal W and suction opening X. The duration and severity of bleeding can be gauged by examining the returning lavage solution.

Thus tamponade may be discontinued at the proper time, preventing unnecessary pressure and the risk of necrosis and ischemia.

In sum, our invention increases the possibility of stopping the bleeding, speeds healing and prevents local infection by the administration of local antibiotics if indicated.

The same procedure may be employed to stop duodenal ulcer bleeding, or bleeding in other tubelike body passages, with the shapes and sizes of the three cuffs and central tube adopted to the size and length of the body passage treated.

It should also be understood that all of the technical procedures in which our invention may be used follow generally accepted practice except to the extent of the procedures described above.

Those skilled in the art may be able to make other modifications and uses of our invention and devise other specific structures for incorporating its principles. It is to be understood that we intend to cover all such changes and modifications which do not constitute a departure from the true spirit and scope of our invention.

What we claim is:

1. A multiple surgical cuff for introduction into an integral body passage comprising:
   (A) A tubular base member having an unblockable lumen;
   (B) A middle cuff member comprising (1) an imperforate inflatable tubular inner cuff member encircling said tubular base member, (2) a distensible tubular outer cuff member encircling said inner cuff member, the wall of said outer cuff member being multiperforated at spaced points;
   (C) First passage means for communicating with the space between said inner cuff member and said outer cuff member for introducing a fluid into said space;
   (D) Second passage means communicating with the space between said inner cuff member and said tubular base member for inflating said inner cuff member to displace wall portions thereof toward the wall of said outer cuff member, whereby the spacing between the opposed walls of said inner and outer cuff members is reduced to transmit fluid outwardly through the perforations of the wall of said outer cuff member or to close said integral body passage;
   (E) A proximal cuff member comprising a first inflatable tubular cuff member encircling said tubular base member on the near side of said middle cuff member;
   (F) Third passage means communicating with the space between said first inflatable tubular cuff member and said tubular base member for inflating said first inflatable tubular cuff member, whereby said proximal cuff member can press against an adjacent body passage portion of said integral body passage;
   (G) A distal cuff member comprising a second inflatable tubular cuff member encircling said tubular base member on the far side of said middle cuff member; p1 (H) Fourth passage means communicating with the space between said second inflatable tubular cuff member and said tubular base member for inflating said second inflatable tubular cuff member, whereby said distal cuff member can press against an adjacent body passage portion of said integral body passage; and (I) Fifth passage means communicating with the space along said tubular base member between said proximal and middle cuff members;

(J) Wherein said middle cuff member, said proximal cuff member and said distal cuff member are permanently located substantially adjacent to each other with respect to said tubular base member;

(K) Whereby, with deflation of said middle cuff member, a continuous flow of fluid may be fed past a body passage portion between said proximal and distal cuff members via said first and fifth passage means.

2. A multiple surgical cuff member according to claim 1 whereby said continuous flow of fluid may be fed through said first passage means into the space between said inner and outer cuff members, then through said multiperforated outer cuff member, then past said body passage portion between said proximal and distal cuff members, and then through said fifth passage means.

3. A multiple surgical cuff according to claim 2 wherein a portion of each of said first, second, third, fourth and fifth passage means passes through the wall of said tubular base member.

4. A multiple surgical cuff according to claim 2 wherein said fifth passage means also functions to introduce a saline solution into the space along said tubular base member between said proximal cuff member and said middle cuff member, or, after deflation of said middle cuff member, to wash out the space between said proximal and distal cuff members.

5. A multiple surgical cuff according to claim 4 wherein said fifth passage means functions to introduce a saline solution, or suck out material, between said distal and proximal cuff members when said middle cuff member is not pressing against the adjacent portion of the wall of the body passage.

6. A multiple surgical cuff according to claim 1 or claim 2 wherein a portion of one or more of said first, second, third, fourth and fifth; passage means passes through the wall of said tubular base member.

7. A multiple surgical cuff according to claim 1 wherein a portion of said tubular base member on the near side of said proximal cuff member comprises a plurality of side window openings, whereby blood may flow through said side window openings into and through said unblockable lumen of said tubular base member.

8. A multiple surgical cuff according to claim 7 wherein a portion of each of said first, second, third and fourth passage means passes through the wall of said tubular base member.

9. A multiple surgical cuff according to claim 7 wherein a portion of each of said first, second, third, fourth and fifth passage means passes through the wall of said tubular base member.

10. A multiple surgical cuff according to claims 1, 2, 5 or 7 wherein said imperforate inflatable tubular inner cuff member and distensible tubular outer cuff member of said middle cuff member have substantially coextensive end portions at one end thereof secured to said tubular base member, and said inner and outer cuff members have the other ends thereof respectively secured to said tubular base member at longitudinally displaced points, whereby said outer cuff member has a greater longitudinal wall extent between the secured ends thereof than that of said inner cuff member so that the wall of said outer cuff member can be selectively positioned in spaced or sealing relation to the wall of the adjacent portion of the body passage.

* * * * *